United States Patent [19]

Gillings

[11] 4,302,189
[45] Nov. 24, 1981

[54] DENTURE RETENTION

[75] Inventor: Barrie R. D. Gillings, Sydney, Australia

[73] Assignee: University of Sydney, Sydney, Australia

[21] Appl. No.: 134,226

[22] Filed: Mar. 26, 1980

[30] Foreign Application Priority Data

Mar. 29, 1979 [AU] Australia ............................ PD8216

[51] Int. Cl.³ ............................................ A61C 13/22
[52] U.S. Cl. .................................................. 433/189
[58] Field of Search ................................ 433/189, 172

[56] References Cited

U.S. PATENT DOCUMENTS

| 2,149,048 | 2/1939 | Freedman | 433/189 |
|---|---|---|---|
| 2,543,773 | 3/1951 | Goldschmidt | 433/189 |
| 2,555,403 | 6/1951 | Freedman | 433/189 |
| 2,709,301 | 5/1955 | Goldsmith | 433/189 |
| 2,803,879 | 8/1957 | Cook | 433/189 |
| 3,798,770 | 3/1974 | Mitchell | 433/189 |
| 4,184,252 | 1/1980 | Krol et al. | 433/172 |
| 4,209,905 | 7/1980 | Gillings | 433/189 |

FOREIGN PATENT DOCUMENTS 2393565  2/1979  France ............................ 433/189

Primary Examiner—Robert Peshock
Attorney, Agent, or Firm—Owen, Wickersham & Erickson

[57] ABSTRACT

A denture is fitted with a U-shaped magnet element which provides for enhanced denture retention by coupling magnetically with a magnetizable element which is located in a decoronated tooth or dental implant in the mouth of a person to whom the denture is fitted. The magnet element is substantially totally enclosed within a base of the denture but pole caps are mounted to respective pole faces of the magnet element and are exposed to engage in abutting contact with the magnetizable element. The pole caps are formed from ferromagnetic stainless steel and function to protect the magnet element from chemical attack and/or mechanical damage in the oral environment.

6 Claims, 6 Drawing Figures

DENTURE RETENTION

FIELD OF THE INVENTION

This invention relates to the construction and retention of dentures.

BACKGROUND OF THE INVENTION

U.S. patent application Ser. No. 904,421, filed May 10, 1978 and now U.S. Pat. No. 4,209,905 issued July 1, 1980, by the present applicant, discloses the use of magnet elements for retaining dentures in place. Paired magnet elements are employed, one element of a pair being embedded in the denture and the other element being located in a support associated with the wearer's jawbone. As described in the patent application, the support might comprise a decoronated natural tooth or a dental implant.

In accordance with a preferred aspect of the invention disclosed in the earlier patent application, an inverted U-shaped magnet element is located in the denture and a magnetisable element (rather than a magnet as such) is located in or on a tooth stump which is to be engaged by the denture. When the denture is fitted, pole faces of the magnet abut the magnetisable element so that the magnetisable element bridges the pole faces in the manner of a keeper and so that a closed-loop magnetic circuit is established. Abutment of the magnet and the magnetisable elements is effected for the purpose of establishing maximum retentivity, and a closed loop magnetic circuit is proposed in the interest of reducing leakage flux to the lowest possible order.

However, the establishment of abutting contact between the magnet and magnetisable elements requires that the pole faces at least of the magnet be exposed, and it is now thought by the Inventor that there may be merit in protecting the magnet pole faces against corrosion induced by the oral environment and/or against physical damage to the magnet element.

SUMMARY OF THE INVENTION

The present invention provides a denture fitted with at least one generally U-shaped magnet element, the magnet element being substantially totally enclosed within the denture but having pole caps mounted to respective pole faces thereof and exposed for abutting contact with a magnetisable element when the denture is fitted to a wearer. The magnetisable element which is contacted by the pole caps is fitted to a support which is associated with the jawbone of a person to whom the denture is intended to be fitted. The support may comprise a decoronated natural tooth or a dental implant.

The pole caps are provided for the purpose of capping the magnet pole faces against exposure to the oral environment or mechanical damage, and, at the same time, to provide for closed-loop coupling of the magnet element and the magnetisable element. Preferably, the pole caps are formed from ferromagnetic stainless steel, although other materials which are substantially impervious or resistant to corrosion by oral juices and which provide for a low reluctance path between the pole faces and the magnetisable element may be employed. Such materials may include gold, silver, chromium, nickel or a plastics material such as polytetrafluoroethylene (PTFE). In the case of a material being employed which does not per se exhibit magnetic properties, such material may be alloyed or be otherwise mixed with a ferromagnetic material in the interest of increasing its effective permeability. Depending upon the nature of the material employed in forming the pole caps, the pole caps may be adhered to the pole faces, be coated onto the pole faces, or be electro-deposited onto the pole faces of the magnet element.

The term "magnet element" as used herein is intended to designate an element which per se exhibits a magnetic field. In contrast, the term "magnetisable element" as used herein is intended to designate an element which need not necessarily be a magnet as such but which does exhibit magnetic properties when subjected to the influence of a magnetic field.

The invention will be more fully understood from the following description of a preferred embodiment thereof, the description being given with reference to the accompanying drawings.

DETAILED DESCRIPTION OF THE INVENTION

Figure 1:
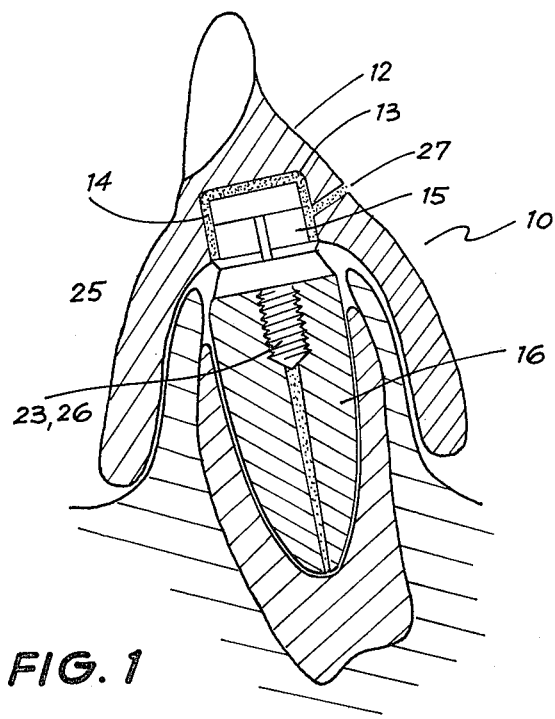
FIG. 1 shows a sectional elevation view of a decoronated mandibular canine tooth stump fitted with a magnetically retained overlay denture.
Figure 2:
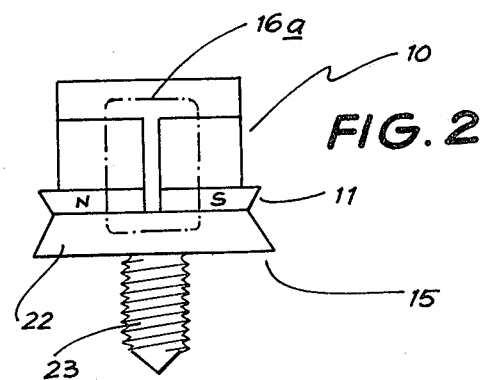
FIG. 2 shows magnet and magnetisable elements which are associated with the arrangement illustrated in FIG. 1.
Figure 3:
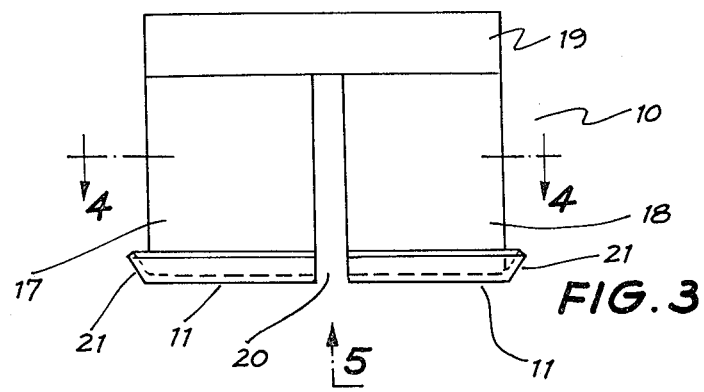
FIG. 3 shows an enlarged elevation view of the magnet element removed from the denture of FIG. 1.
Figure 4:
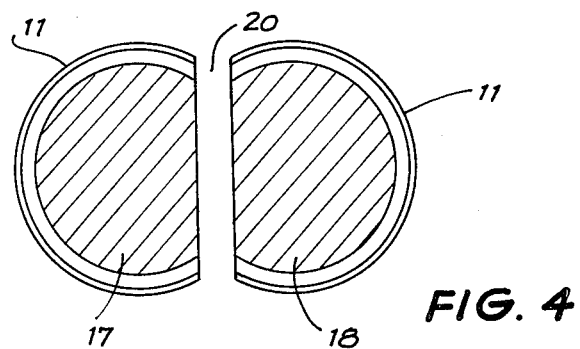
FIG. 4 shows a sectional view of the magnet element as viewed in the direction of section plane 4—4 in FIG. 3.
Figure 5:
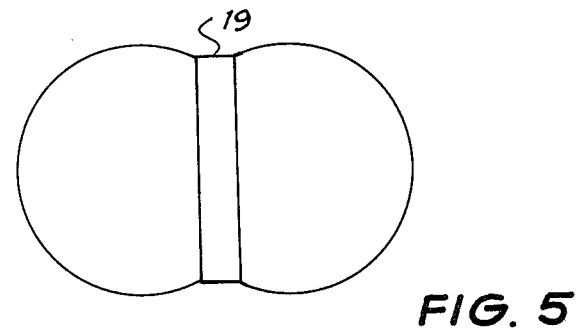
FIG. 5 shows an end elevation of the magnet element as viewed in the direction of arrow 5 in FIG. 3.
Figure 6:
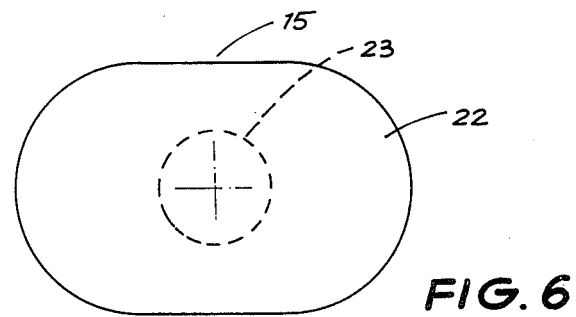
FIG. 6 shows a plan view of the magnetisable element removed from engagement with the tooth stump shown in FIG. 1.

As shown in the drawings, a magnet element 10 which is capped with pole caps 11 is located in an overlay denture 12. The magnet element 10, including the pole caps 11, is held captive in a cavity 13 within the denture by a synthetic resin 14. Also, a magnetisable element 15 is fitted to a tooth stump 16 and, when the denture is fitted to a wearer, the pole caps 11 of the magnet element abut the magnetisable element 15 to establish a closed-loop magnetic circuit as indicated by the line 16a in FIG. 2.

The magnet element 10 comprises two magnet portions 17 and 18, each of which has a cross-section profiled as a major segment of a circle. The two magnet portions 17 and 18 are inverted with respect to one another, so as to be oppositely poled, and they are connected by a ferromagnetic stainless steel bridge 19. Thus, the magnet element 10 is in the form of a U-shaped magnet.

Both of the magnet portions 17 and 18 comprise cobalt-samarium magnets, and they are spaced-apart along their length by an air-gap 20.

The pole faces of the magnet element 10 are capped with the pole caps 11, the pole caps having a thickness in the order of 200 to 600 $\mu$m, being cemented to the pole faces and being separated by the air gap 20. Each of the pole caps 11 is formed from a ferromagnetic stainless steel and has a lip 21 which caps the contacting pole face of the magnet element.

The magnetisable element 15 which is mounted to the tooth stump 16 is formed from ferromagnetic stainless steel and has an upper portion 22 which is configured to match the contacting pole caps of the magnet element 10. Also, a central threaded spigot 23 projects downwardly from the upper portion for screw engagement in a drilled hole in the anchoring tooth stump 16.

One procedure which may be used for fitting the magnet and magnetisable elements 10 and 15 to a patient is now described.

The patient's two manibular canine teeth 16 are root-filled, decoronated, trimmed approximately flush with the gingival margin 25, and formed with a cavity 26. The magnetisable element is then screwed and cemented into the cavity 26 and the magnet element 10 is fitted onto and aligned with the magnetisable element 15.

An impression is then taken from the patient with the magnet elements 10 in place, the magnet elements are removed from the impression for later use in the denture, and a cast is prepared from the impression. The overlay denture 12 is then constructed for the patient using the cast, the holes left by the magnet elements which were removed from the impression being preserved in the denture base and thereafter being enlarged slightly to form the cavities 13. The magnet elements 10 are then reseated on the magnetisable elements 15 in the patient, as at the commencement of the procedure, and the denture 12 is then positioned in the patient's mouth and over the magnet elements. A cold-curing acrylic resin is then injected into the denture base, by way of pre-drilled apertures 27, to surround and secure the magnet elements 10. After curing of the resin, the denture (including the magnet elements 10) is removed and any excess resin is trimmed from the tissue-conforming surface of the denture.

As an alternative procedure, a form of the well-known "transfer coping technique" may be employed for fabricating the overlay denture, such technique being modified to use the magnet element 10 as the coping.

To ensure accurate reseating of the denture to the magnetisable elements 15, such keeper elements may each be formed with a geometrical locating projection. The projection is preferably positioned to align and locate in the airgap groove 20 of the magnet element 10.

Variations and modifications may be made in respect of the above described arrangement without departing from the scope of the invention as set forth in the following statements of claim.

I claim:

1. A denture comprising a base having a gum tissue conforming surface, at least one artificial tooth mounted to the base, and at least one magnet element located in the base; the magnet element comprising a generally U-shaped magnet of strongly magnetic material and having spaced-apart pole faces which are disposed in a common plane, the magnet element being substantially totally enclosed within the denture base and having very thin pole caps located on the respective pole faces thereof, the pole caps being exposed at the tissue conforming surface of the denture base for engaging in abutting contact with a magnetisable element when the denture is fitted to a wearer, and the pole caps being formed from a material which exhibits magnetic permeability and which is substantially resistant to corrosion by oral juices.

2. A denture as claimed in claim 1 wherein each pole cap comprises a ferro-magnetic material.

3. A denture as claimed in claim 1 wherein each pole cap is formed from ferro-magnetic stainless steel and is about 200 to 600 $\mu$m thick.

4. A denture as claimed in claim 3 wherein each pole cap is secured to its associated pole face of the magnet element by an adhesive.

5. A denture as claimed in claim 3 where the magnet pole faces have a cross-sectional area configured as a major sector of a circle and wherein each pole cap is formed with a lip which extends around an arcuate portion of the associated pole face.

6. A denture as claimed in claim 1 in combination with a said magnetisable element, the magnetisable element being formed from a ferro-magnetic material and being engagable by both of the pole caps of the associated magnet element, and the magnetisable element having a spigot portion for location in a support associated with the jawbone of a person who is to be fitted with the denture.

* * * * *